United States Patent [19]

Lai

[11] Patent Number: 4,473,694

[45] Date of Patent: Sep. 25, 1984

[54] PROCESS FOR THE PREPARATION OF POLYSUBSTITUTED α-AMINOACETAMIDES

[75] Inventor: John T. Lai, Broadview Heights, Ohio

[73] Assignee: The B. F. Goodrich Company, Akron, Ohio

[21] Appl. No.: 427,321

[22] Filed: Sep. 29, 1982

Related U.S. Application Data

[63] Continuation-in-part of Ser. No. 250,826, Apr. 3, 1981, abandoned.

[51] Int. Cl.$^3$ ............... C07D 401/12; C07D 413/12; C07D 211/32; C07D 241/04
[52] U.S. Cl. ................... 546/247; 546/190; 546/233; 544/82; 544/86; 544/357; 544/168; 544/400; 564/197; 564/194; 564/168; 564/167; 564/163; 564/189; 564/190; 564/191; 564/159; 564/160; 564/157
[58] Field of Search ............... 564/197, 194, 168, 167, 564/163, 189, 190, 191, 159, 160, 157; 544/82, 86, 357, 168, 400; 546/233, 190, 247

[56] References Cited

U.S. PATENT DOCUMENTS

| | | | |
|---|---|---|---|
| 4,080,452 | 3/1978 | Malen et al. | 564/194 |
| 4,237,068 | 12/1980 | Boyes et al. | 564/194 |
| 4,252,804 | 2/1981 | Joullie et al. | 564/194 |
| 4,310,429 | 1/1982 | Lai | 564/194 |

Primary Examiner—John M. Ford
Attorney, Agent, or Firm—Nestor W. Shust; Carl W. Battle; George A. Kap

[57] ABSTRACT

Process for the synthesis of hindered polysubstituted α-amino acetamides which comprises first reacting an α-haloacetamide with a base to form an intermediate α-lactam which in turn is reacted with a primary or secondary amine. The product thus obtained can comprise a multifunctional compound having one or more hindered amino moieties. These compounds are highly effective as UV stabilizers in a variety of plastics, especially the alpha monoolefins.

4 Claims, No Drawings

PROCESS FOR THE PREPARATION OF POLYSUBSTITUTED α-AMINOACETAMIDES

CROSS-REFERENCE TO RELATED APPLICATIONS

This is a continuation-in-part of my copending application Ser. No. 250,826, filed Apr. 3, 1981, now abandoned.

BACKGROUND OF THE INVENTION

1. Field of the Invention—This invention relates to a process. More specifically, this invention is directed to the synthesis of hindered amines by base-induced condensation of a primary or secondary amine with an α-halo-acetamide.

2. Description of the Prior Art—The increasing use of polymers in the place of the more traditional types of structural materials, (e.g. wood, metals, etc.) has necessitated the compounding of such polymers with a variety of stabilizers in order to enhance their ability to withstand prolonged exposure to a variety of degradative forces. Degradation of such environmentally sensitive polymers can be caused by exposure to light, heat and/or air. Such degradation is usually manifest by either a partial or total loss of structural integrity, changes in light transmission properties, changes in color, loss or reduction in flexibility and/or resiliency, or any combination of the above phenomenon. As will be appreciated, the stabilizers which are used in conjunction with the above polymeric materials, in addition to providing protection against such degradative forces, must also be compatible with the aesthetic properties of the polymeric article formed from such materials and be effective at low concentrations. The economics of the marketplace dictate that these stabilizers be relatively inexpensive and capable of preparation from readily available starting materials by simple and straightforward synthesis techniques.

The prior art is replete with both patents and technical articles describing various stabilizers suitable for use in structural/engineering plastics and in various synthetic fibers. The hindered amine stabilizers are prominently mentioned as suitable in the stabilization of such materials against ultraviolet light degradation. Illustrative of these hindered amines are the decahydroquinolines disclosed in U.S. Pat. Nos. 3,919,234; 3,920,659; 3,928,330; 4,069,195; and 4,073,770; the 1,5-diazacycloalkan-2-ones disclosed in U.S. Pat. No. 4,207,228; and, the 1,4-diazacycloalkan-2-ones disclosed in U.S. Pat. Nos. 4,167,512 and 4,240,961. These hindered amine stabilizers can be prepared in various ways and from various materials.

The preparation of the U.V. stabilizers disclosed in U.S. Pat. Nos. 4,240,961 and 4,190,571 is reportedly achieved by phase transfer catalyzed reaction of certain appropriate starting materials. Phase transfer catalysis initiated synthesis is also reportedly effective in the synthesis of other types of stabilizer; namely, the synthesis of antioxidants and compounds which enhance a polymer's resistance to thermal degradation.

The first disclosure relating to the phase transfer catalyzed synthesis of this latter class of stabilizers is described in copending patent application Ser. No. 916,639 filed June 19, 1978. The compounds are prepared by a reaction of aniline, and its para-substituted derivatives, with chloroform, acetone and sodium hydroxide in the presence of a phase transfer catalyst.

The synthesis proceeds by the reaction of chloroform with base thereby generating a trichloromethide ion which can subsequently combine with the ketone (or aldehyde) forming an oxirane intermediate. This intermediate combines with the aniline, or its para-substituted derivatives, and optionally, with another primary or secondary amine yielding the desired reaction product.

SUMMARY OF THE INVENTION

This invention deals with a process for the synthesis of polysubstituted α-aminoacetamides of the formula

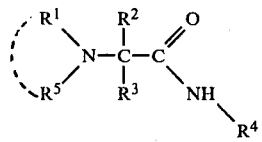

wherein $R^1$ and $R^4$ are independently selected from the group consisting of alkyl of 1–8 carbon atoms, aryl, cycloalkyl of 4 to 8 carbon atoms, piperidinyl, hindered piperidinyl and alkalene of 2–6 carbon atoms, or $R^4$ is hydrogen or $R^4$ is an alkylene α-aminoacetamide resulting in a bis compound; $R^2$ and $R^3$ are independently selected from the group consisting of hydrogen and alkyl of 1–6 carbon atoms; and $R^5$ is hydrogen or alkyl of 1–6 carbon atoms and can, in conjunction with the acyclic substituents of $R^1$, form a heterocyclic group pendant from the α-carbon.

The process comprises reacting, in the presence of a base, a primary or secondary amine with an α-halo-acetamide. The terms "asymmetrical" and "symmetrical" as employed herein in the characterization of the substituted acetamide refers to similarity or dissimilarity in the substitutents pendent from and/or which include the nitrogen atoms at the opposite ends of such compounds. These compounds are useful in the stabilization of photosensitive polymers against the degradative action of ultraviolet light.

DETAILED DESCRIPTION

The instant invention is directed to a process for the preparation of polysubstituted α-aminoacetamides having the formula

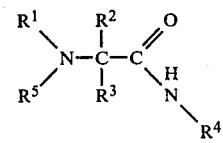

wherein $R^1$ and $R^4$ are independently selected from the group consisting of alkyl of 1 to 8 carbons; phenyl; alkyl-, alkoxy-, alkylamino-, dialkylamino- or halo-substituted phenyl having 1 to 3 said substitutents wherein alkyl groups have 1 to 12 carbons; cycloalkyl of 4 to 8 carbons; piperidinyl; 2,2,6,6-tetra(lower alkyl)piperidinyl; alkenyl of 2 to 6 carbons, or $R^4$ is hydrogen or $R^4$ is a group

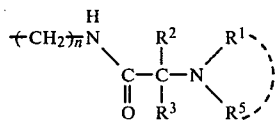

where n is 1 to 6; $R^2$ and $R^3$ are independently selected from the group consisting of hydrogen and alkyl of 1 to 6 carbons; and $R^5$ is hydrogen or alkyl of 1 to 6 carbons and $R^1$ and $R^5$ together with the nitrogen form a heterocyclic ring selected from the group consisting of piperidine, morpholine, and piperazine.

The groups $R^1$ and $R^4$, as stated above, may be a phenyl which is substituted with 1 to 3 substituents. Such substitutents may be alkyl, alkoxy, alkylamino, dialkylamino or halo groups. When the substitutent contains an alkyl group the alkyl has preferably 1 to 6 carbon atoms. The halo substitutents are preferably chlorine or bromine. When $R^1$ and $R^4$ are cycloalkyl they preferably contain 5 to 7 carbons. When such groups are tetra(lower alkyl)piperidinyl, the lower alkyl have 1 to 4 carbons and preferably methyl. When $R^4$ is alkenyl it is meant that it can be a monoethylenically unsaturated group. Illustrative examples of such groups are ethenyl, propenyl, butenyl-1, butenyl-2, isobutenyl, pentenyl-1, 3-methylbutenyl-1, hexenyl-1 and the like. $R^4$ can also be the group

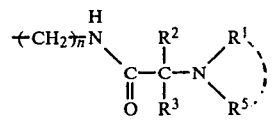

In such a case the resulting compounds are alkylene bis(α-aminoacetamides).

Although most of the compounds prepared by the process of this invention are known, a certain class of compounds is new. Such novel compounds are where
  $R^5$ is hydrogen,
  $R^1$ is tert-alkyl of 4 to 12 carbons, and
  $R^2$, $R^3$ and $R^4$ are as defined above.
The $R^1$ group is the critical group in the novel compounds. Being tertiary alkyl, it is a highly hindering group. Such compounds could not be prepared by prior art methods. These tert-alkyl groups have preferably 4 to 8 carbons and preferably $R^1$ is tert-butyl and tert-octyl. Illustrative examples of such groups are t-butyl, t-octyl, t-nonyl, 2,4,4-trimethyl-2-pentyl, 2-methyl-2-heptyl, 2,4,4-trimethyl-2-hexyl, 2,4,4-trimethyl-2-heptyl and the like. The most relevant prior art reference pertaining to this new class of compounds is Langyel et al., *Angew. Chem. Internat. Ed.*, 7, 25(1968) which discloses the preparation of benzylamino-compounds instead of the tert-alkyl compounds.

The primary and secondary amines suitable for use in this process can be represented by the following formula:

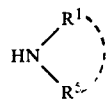

wherein $R^1$ and $R^5$ as defined above.

Representative of the primary and secondary amines which are within the scope of the foregoing formula and suitable for use in the process of this invention include: primary amines such as t-butylamine, t-octylamine, aniline, alkyl substituted aniline (i.e. toluidine), isopropyl amine, propyl amine, 4-amino-2,2,6,6-tetramethyl-piperidine, allyl amine; and, secondary amines such as morpholine, N-methyl-aniline, diethyl amine.

The α-halo-acetamides suitable for use in the process of this invention can be represented by the following formula:

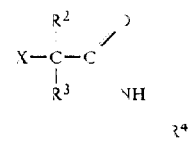

wherein $R^2$, $R^3$ and $R^4$ are as defined above. In addition, $R^4$ may be

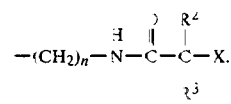

Representative of the α-halo-acetamides which are within the scope of the foregoing formula and suitable for use in the process of this invention include: α-chloro-α,α-dimethyl-N-phenylacetamide, α-bromo-α,α-dimethyl-N-phenylacetamide, α-bromo-α,α-dimethylacetamide, N,N'[1,2-ethane-bis (α-bromo-α,α-diethyl acetamide)], and α,bromo-α,α-dimethyl-N-(2,2,6,6-tetramethyl-4-piperidinyl) acetamide.

The overall synthesis involved in the process of this invention involves initially charging a reactor, under the conditions hereinafter set forth with an appropriate amine, an α-halo-acetamide and base (i.e., an alkali metal hydroxide) and thereafter heating the contents of the reactor for a predetermined interval. The synthesis proceeds generally as follows:

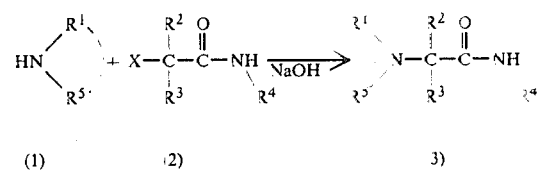

(1)   (2)   (3)

Although the foregoing reaction appears straight forward, the various reactants initially combine with one another to form certain intermediate compounds, which in turn react with one another to form the desired product. It is in the formation of these intermediate compounds which distinguishes this process from that previously disclosed in the copending application, Ser. No. 916,639.

Initially, the α-haloacetamide, referred to hereinabove, reacts with the sodium hydroxide to produce an α-lactam intermediate:

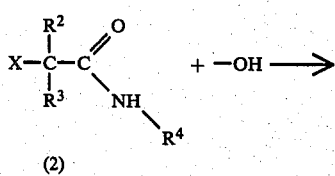

(2)

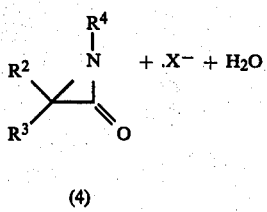

(4)

This intermediate species differs significantly from the oxirane intermediate of the process previously disclosed by Lai in that the above α-lactam has only one potentially reactive site for addition of the primary or secondary amine. Therefore, this α-lactam and the primary and secondary amines set forth hereinabove, can only react with one another as follows:

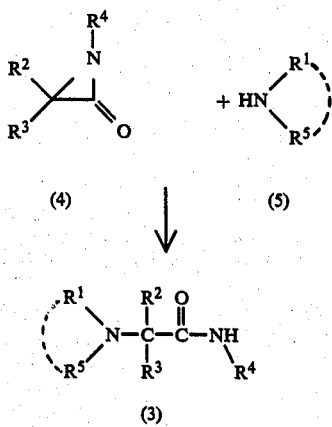

As is apparent, the above series of reactions permits the formation of both symmetrical and asymmetrical compounds; does not lead to the formation of product mixture since the imino-α-lactone is only reactive toward the primary and secondary amine at a single site, the tertiary carbon; the reaction requires less base for the neutralization of the mineral acid formed incidental to the α-lactam formation; and the reaction is decidedly less exothermic thereby permitting greater freedom of process control. By way of comparison, it will be appreciated that since the reaction of the α-lactam intermediate with aniline, and substituted aniline, proceeds spontaneously in the presence of base, the reaction temperature must be carefully controlled; the reaction temperature being preferably maintained between 0° to 10° C. In contrast to the above, the α-lactam intermediate, produced during the process of this invention, reacts only sluggishly with both the primary and secondary amine under ambient laboratory conditions and requires heating of the reactor charge, to a temperature in the range of from about 20° to 100° C. to drive the reaction, at an acceptable rate, in the direction of the desired product. Preferably the reaction temperature is 40°-100° C., but it depends on the reactivity of the amine.

In the process of this invention, the relative concentration of the reactants to one another, and process conditions of this synthesis should be adequate to insure both a satisfactory rate of reaction and acceptable product yield. In general, the relative molar concentration of primary or secondary amine to α-halo-acetamide can range from about 1:1 to about 100:1 and preferably 1.2:1 to 20:1. In the preferred embodiments of this invention, a stoichiometric excess of primary or secondary amine is required to drive the reaction in the direction of the desired product. The concentration of NaOH (present as a 50% aqueous solution, or preferably in solid form) is generally not critical so long as sufficient base is present to transform the α-halo-acetamide to the corresponding -α-lactam and neutralize the mineral acid generated during the intermediate phase of the reaction. Good results have been obtained where the molar concentration of NaOH (based upon solid form) relative to α-halo-acetamide in the original charge, is in the range of from about 1:1 to 1:5. This relationship, of course, is somewhat misleading since the NaOH is preferably added incrementally to the reactor after all the reactants have been charged to the reactor. The reaction time is generally from 1 to 10 hours, depending on the reactivity of the amine.

Typically, the foregoing reactants are added to a reactor, such as a round-bottomed flask equipped with a reflux condenser, the reactor purged of air with an inert gas, and powdered NaOH added incrementally while the exotherm of the reaction is initially controlled by immersion of the base of the flask in an ice bath. The reactor is also preferably equipped with a magnetic stirrer. The conditions prevailing during such process can be readily controlled and generally the reaction proceeds at atmospheric pressure. The reaction can proceed satisfactorily at temperatures in the range of from about 20° C. to about 100° C., and most preferably from 40° C. to 100° C.

Often times one or more of the reactants themselves (i.e., the primary or secondary amine) can serve as the medium for the conduct of the synthesis of this invention. Alternatively, such synthesis can also be satisfactorily conducted in an organic solvent; provided, such solvent is inert toward both the reactants and product of the synthesis under the anticipated reaction conditions. Typical organic solvents which can be used in this process include the common aromatic and paraffinic solvents such as benzene, p-xylene, toluene, dichloromethane, chlorobenzene, cyclohexane and the like.

Once the desired compound has been prepared from the aforementioned materials in accordance with the above process, it can be readily recovered from the reaction medium by conventional means.

The compounds prepared as described above are highly effective in the stabilization of photodegradable polymeric material from the deteriorating effects of ultraviolet light.

The term "photodegradation" as used herein is intended as descriptive of any photo-induced changes in the physical, chemical and/or electrical properties of such organic polymeric materials upon their exposure to sufficient quanities of ultra-violet light. Such degradation can typically include cross-linking of the polymer, dehydrohalogenation, reduction in chain length, photooxidation and the like. Polymers which are especially sensitive to ultraviolet light degradation are materials which contain unsaturation along their respective backbones, such as cispolyisoprene, styrene/butadiene copolymer, vinyl halide polymers, polyolefins, polyacetaldehydes, polyurethanes, ABS resins, polystyrene, polyacrylonitrile, polycarbonates, polyacrylates, poly-α-alkyl-acrylates, varnish, phenolformaldehyde resins, polyepoxides, polyesters, and their respective blends and copolymers. The compounds prepared according to the process of this invention are especially effective in the stabilization of the poly-α-monoolefins such as polymers derived from ethylene, propylene, isobutylene, 1-butene, 1-pentene, 1-hexene, 4-methyl-1-pentene and the like.

In addition to the stabilizers prepared according to the process of this invention, a typical structural/engineering plastic can contain common compounding ingredients and additional stabilizers for the protection of such plastic against various other degradative forces and agents.

Representative compounding ingredients can include metal oxides, such as zinc, calcium and magnesium oxide, fatty acids such as stearic, lauric acid and the metal salts thereof; fillers such as calcium and magnesium carbonate, calcium and barium sulfonates, aluminum silicates, asbestos, and the like; plasticizers and extenders, such as dialkyl and diaryl organic acids, such as diisobutyl, diisooctyl, diisodecyl and dibenzyl oleates, stearates, sebacates, azelates, phthalates, and the like; ASTM Type 2 petroleum oils, paraffinic oils, castor oil, tall oil, glycerine, and the like; antioxidants, such as 2,6-di-t-butyl phenol), 2,2'-thio-bis-(4-methyl-6-t-butyl phenol), 2,2'-methylene-bis-6-t-butyl-4-ethyl phenol, 4,4'-butyldiene-bis-6-t-butyl-m-cresol, 2-(4-hydroxy-3,5-di-t-butylanilino-4,6-bis(octylthio)1,3,5-triazine, hexahydro-1,3,5-tris-β-(3,5-di-t-butyl-4-hydroxybenzyl)-isocyanurate, tetrakismethylene-3(3',5'-di-t-butyl-4'-hydroxyphenyl) propionate methane, distearylthiodipropionate, dilaurylthiodipropionate, tri(nonylphenyl) phosphite, tin thioglycolate, and the like; and other ingredients such as pigments, tackifiers, flame retardants, fungicides, and the like.

Additional stabilizers which are especially preferred for use in combination with UV stabilizer, prepared as described herein, are the antioxidants. The inclusion within the polymer composition of an antioxidant, in addition to the UV stabilizer, confers upon the polymer composition stability against two of the more environmentally hostile degradative forces. The antioxidant can be present within the polymer composition within the range of from about 0.1 to about 10 parts by weight per 100 parts by weight polymer, and preferably from about 0.2 to about 5 parts by weight per 100 parts by weight of polymer. Generally, the phenolic antioxidants are preferred for use in conjunction with the UV stabilizer of this invention.

Examples of phenolic antioxidants are 2,6-di-t-butylphenol; 2-methyl-4,6-dinonyl phenol; 2,6-di-t-butyl-p-cresol; 2,2'-methylenebis (4-methyl-6-t-butyl phenol); 1,1'-methylenebis (2-naphthol); 4,4'-methylenebis (2,6-di-t-butyl phenol); 4,4'-thiobis(6-t-butyl-m-cresol); and the like. Some of the more common and popular of the phenolic anti-oxidants are the esters having alkylhydroxyphenyl substituents; trazines having alkylhydroxyphenyl substituents; and isocyanurates having alkylhydroxyphenyl substituents.

Examples of phenolic antioxidants having alkylhydroxyphenyl substituents on an ester nucleus are disclosed in U.S. Pat. Nos. 3,330,859 and 3,627,725 and exemplified by di-lauryl α,α'-bis(3,5-di-t-butyl-4-hydroxybenzyl)malonate; compounds exemplified by tetrakis(methylene-3-(3',5'-di-t-butyl-4'-hydroxyphenyl) propionate)methane; and the like.

Examples of phenolic antioxidant compounds having alkyhydroxyphenyl substituents on a heterocyclic nucleus are triazine compounds such as disclosed in U.K. Pat. No. 977,589 and exemplified by 2,4,6-tris(4-hydroxy-3,5-di-t-butyl benzylthio)-1,3,5-triazine; disclosed in U.S. Pat. No. 3,706,740 and exemplified by 2,4,6-tris(3',5'-di-t-butyl-4'-hydroxybenzyl)-1,3,5-triazine; disclosed in U.S. Pat. No. 3,567,724 and exemplified by hexahydro-1,3,5-tris-β-(3,5-di-t-butyl-4-hydroxyphenyl)propionyl-s-triazine; disclosed in U.S. Pat. No. 3,694,440 and exemplified by 1,3,5-tris(4'-hydroxy-3',5'-di-t-butylphenylpropionyloxyethylthiopropionyl)hexahydro-1,3,5-triazine; and the like.

Examples of phenolic antioxidant compounds having alkylhydroxyphenyl substituents on an isocyanurate nucleus are disclosed in U.S. Pat. No. 3,531,483 and exemplified by tris-(3,5-di-t-butyl-4-hydroxybenzyl)isocyanurate; disclosed in U.S. Pat. No. 3,678,047 and exemplified by 2,2',2"-tris(3,5-di-t-butyl-4-hydroxyphenyl)propionyloxy) ethyl isocyanurate; and the like.

Still other hindered phenols useful as thermal antioxidants are disclosed in U.S. Pat. No. 3,920,659, and in copending U.S. patent application Ser. No. 697,345 and Ser. No. 697,387 which are incorporated herein by reference as if fully set forth.

Ordinarily, a structural/engineering grade resin can be compounded with the various types of stabilizer materials described hereinabove in accord with standard mixing techniques and equipment; such as in a Banbury mixer, a Henschel mixer, a rubber mill, an extruder mixer or equivalent device. The various components of the composition may be physically intimately blended either in the absence of or in the presence of a common solvent; or in a solvent which is capable of dissolving the polymer component of the composition yet substantially incapable of dissolving the stabilizer ingredients. Typical of such solvent/dispersing agents include hexane or benzene. Subsequent to intimately dispersing the various components of the composition within one another, the dispersing agent (if any) can be removed by selective evaporation and the resultant resin recovered. The resin may thereafter be formed into useable products by a variety of standard techniques.

The ultra-violet light stability of the compositions of this invention is evaluated by exposing samples of a photosensitive plastic, with and without stabilizer, to a Xenon or carbon arc light in a Weather-Ometer operating at temperatures of about 60° C. The sample is considered to have been photodegraded when it has lost in excess of fifty percent (50%) of its tensile strength as determined by ASTM D 638-76. In a typical test protocol, a pre-selected quantity of UV stabilizer, antioxidant and other optional processing aids (if any) are compounded with an unstabilized photosensitive resin, such as polypropylene, and the compounded resin compression molded into sheets approximately 20 mils in thickness. Several sheets of plastic are usually prepared in the above manner, each having different stabilizers, at different concentrations. Subsequent to formation of the foregoing compounded resin into sheet material, a series of dumb bells are cut from each sheet and placed in a Weather-Ohmeter. At 500 hours, or other pre-selected intervals, one (1) dumb bell of each sample of compounded resin is removed from the Weather-Ohmeter and its tensile strength measured on an Instron tensile testing device. The tensile strength of each sample is then compared to the values obtained from a sample cut from the same sheet which had not experienced any UV exposure. The sample is considered to have been photodegraded when it has experienced in excess of fifty percent (50%) reduction in its tensile strength.

EXAMPLES

The Examples which follow further define, describe and illustrate the (i) process for the synthesis of polysubstituted α-amino-acetamide and (ii) evaluation of the stabilizer properties of the compounds obtained in such synthesis. Apparatus and procedures used in the foregoing process and evaluation of such samples are standard or as hereinbefore described. Parts and percentages appearing in such examples are by weight unless otherwise stipulated.

EXAMPLE I

Preparation of α-(t-butylamino)isobutyramide

A three necked round bottomed flask, equipped with a reflux condensor, magnetic stirrer and a thermometer, is initially chilled by immersion of its base in an ice bath, and thereafter charged with 100 mmoles t-butylamine, 5 mmoles α-bromo-isobutyramide.

The flask is purged of air with an inert gas, such as argon, and 10 mmoles of powdered NaOH added in small portions to the charge over a period of ten minutes. After this initial period, the exotherm of the reaction plateaus. The contents of the flask are then heated and allowed to react for 4 hours under refluxing conditions with mild agitation. Heating is thereafter discontinued, the contents of the flask diluted with methylene chloride and the solids removed by filtration. The solids are thereafter washed with methylene chloride. Concentration of the filtrate yielded the product which could be further purified by recrystallization. Spectral and elemental analysis of the recovered product thus obtained are consistent with the structure of the title compound.

EXAMPLES II–XII

The procedures of Example I are repeated except for substitution of one or more, of the following reactants of Table I for those employed in Example I:

TABLE I

| EX. NO. | α-halo-acetamide | 1° or 2° amine | Yield (%) | mp (°C.) |
|---|---|---|---|---|
| II | α-chloro-α,α-dimethyl-N—phenylacetamide | t-butylamine | 80 | 17.5–79 |
| III | α-bromo-α,α-dimethyl-N—phenylacetamide | t-butylamine | 82 | 77–79 |
| IV | α-bromo-α,α-dimethyl-N—t-butylacetamide | t-butylamine | 65 | 70–72 |
| V | α-bromo-α,α-dimethyl-acetamide | t-butylmine | 55 | 110.5–113 |
| VI | N,N'1,2-ethane-bis(α-chloro-α,α-dimethylacetamide) | t-butylamine | 80 | 96.5–98.5 |
| VII | α-bromo-α,α-dimethyl-N—2,2,6,6-tetramethyl-4-piperidinylacetamide | t-butylamine | 85 | 139–141 |
| VIII | α-bromo-α,α-dimethyl-N—2,2,6,6-tetramethyl-4-piperidinylacetamide | phenylamine | 84 | 163–164 |
| IX | α-bromo-α,α-dimethyl-N—t-butylactamide | phenylamine | 71 | 140–142 |
| X | α-bromo-α,α-dimethyl-N—t-butylacetamide | morploline | 52 | 64–67 |
| XI | α-bromo-α,α-dimethyl-N—2,2,6,6,-tetramethyl-4-piperidinylacetamide | 4-amino-2,2,6,6-tetramethyl piperidine | 69 | 125–6 |
| XII | N',N—1,2-ethane-bis-(α-chloro-α,α-tetramethylene-acetamide) | t-butylamine | 45 | 174–7 |

(*percentage based upon isolated product)

EXAMPLE XIII–XVIII

In order to ascertain the effectiveness as UV stabilizer of compounds prepared in accordance with the process of this invention, certain representative UV stabilizers are compounded with an unstabilized polypropylene resin, along with an antioxidant (GOODRITE 3125), compression molded into sheets approximately 20 mils thick and tested in a Weather-Ohmeter in the manner previously described. Table II, which follows, indicates the comparative effectiveness of the UV stabilizers subjected to such testing and further compares their performance to an unstabilized sample of the same resin.

TABLE II

| Ex. No. | Compound of** | Failure of Sample* |
|---|---|---|
| XIII | Example VII | 1500 |
| XIV | Example VIII | 1200 |
| XV | Example VI | 1000 |
| XVI | Example XI | 1850 |
| XVII | Example V | 650 |
| XVIII | Control, (contains only antioxidant) | 180 |

*Sample considered to have failed upon loss of in excess of 50% of its tensile strength.
**All stabilizer compounds present in sample at concentration of 0.125 phr (parts per 100 parts resin); and antioxidant present at concentration of 0.10 phr (parts per 100 parts resin).

All of the stabilized films compare favorably, in terms of their resistance to photodegradation, to the unstabilized control.

The foregoing Examples have been provided as illustrative of a number of the preferred embodiments of this invention and are not intended for delineation of the scope thereof which is set forth in the following claims:

I claim:

1. A process for the preparation of polysubstituted α-aminoacetamides having the formula

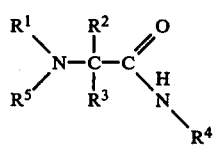

wherein $R^1$ and $R^4$ are independently selected from the group consisting of alkyl of 1 to 8 carbons; phenyl; alkyl-, alkoxy-, alkylamino-, dialkylamino- or halo-substituted phenyl having 1 to 3 said substitutents wherein alkyl groups have 1 to 12 carbons; cycloalkyl of 4 to 8 carbons; piperidinyl; 2,2,6,6-tetra(lower alkyl)piperidinyl; alkenyl of 2 to 6 carbons, or $R^4$ is hydrogen or $R^4$ is a group

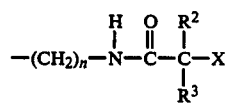

where n is 1 to 6; $R^2$ and $R^3$ are independently selected from the group consisting of hydrogen and alkyl of 1 to 6 carbons; and $R^5$ is hydrogen or alkyl of 1 to 6 carbons or $R^1$ and $R^5$ together with the nitrogen form a heterocyclic group selected from the group consisting of piperidinyl, morpholinyl and piperazinyl, said process comprises (a) reacting an α-haloacetamide of the formula

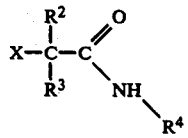

wherein $R^2$, $R^3$ and $R^4$ are as defined above or $R^4$ is

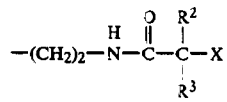

and X is chlorine or bromine; with a stoichiometric amount of a base selected from the group consisting of sodium hydroxide and potassium hydroxide, to form an intermediate α-lactam, and thereafter (b) reacting said intermediate α-lactam with an amine of the formula

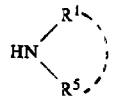

wherein $R^1$ and $R^5$ are as defined above, said reaction being carried out in an inert atmosphere, at a temperature of from 20° C. to about 100° C. and the molar ratio of an amine to an α-haloactamide being in the range of from 1:1 to 100:1.

2. A process of claim 1 wherein the molar ratio of an amine to an α-haloacetamide is in the range of from 1.2:1 to 20:1.

3. A process of claim 1 wherein the amine is selected from the group consisting of t-butylamine, t-octylamine, aniline, alkyl substituted aniline, isopropyl amine, propyl amine, 4-amino-2,2,6,6-tetramethyl-piperidine, allyl amine, morpholine, N-methyl-aniline, and diethyl amine.

4. A process of claim 1, wherein the α-halo-acetamide is selected from the group consisting of α-chloro-α,α-dimethyl-N-phenylacetamide, α-bromo-α,α-dimethyl-N-phenylacetamide, α-bromo-α,α-dimethyl-N-(t-butyl)acetamide, α-bromo-α,α-dimethylacetamide, N,N'[1,2-ethane-bis(α-bromo-α,α-diethyl acetamide)], and α-bromo-α,α-dimethyl-N-(2,2,6,6-tetramethyl-4-piperidinyl) acetamide.

* * * * *